US008844367B2

(12) United States Patent
Takashima et al.

(10) Patent No.: US 8,844,367 B2
(45) Date of Patent: Sep. 30, 2014

(54) MICROMATERIAL STRAIN MEASUREMENT APPARATUS AND METHOD THEREFOR

(75) Inventors: Kazuki Takashima, Kumamoto (JP);
Masaaki Otsu, Kumamoto (JP);
Mitsuhiro Matsuda, Kumamoto (JP);
Hiroaki Kurahara, Kumamoto (JP);
Hidetaka Maeda, Hidaka (JP);
Tadahiro Yonekura, Hidaka (JP)

(73) Assignee: Kumamoto University, Kumamoto-shi, Kumamoto (JP)

( * ) Notice: Subject to any disclaimer, the term of this patent is extended or adjusted under 35 U.S.C. 154(b) by 0 days.

(21) Appl. No.: 13/701,402

(22) PCT Filed: Jun. 1, 2011

(86) PCT No.: PCT/JP2011/062565
§ 371 (c)(1),
(2), (4) Date: Nov. 30, 2012

(87) PCT Pub. No.: WO2011/152441
PCT Pub. Date: Dec. 8, 2011

(65) Prior Publication Data
US 2013/0068034 A1 Mar. 21, 2013

(30) Foreign Application Priority Data
Jun. 2, 2010 (JP) ................................. 2010-127109

(51) Int. Cl.
*G01L 1/24* (2006.01)
*G01N 3/08* (2006.01)
*G01B 11/16* (2006.01)
*G01N 3/06* (2006.01)

(52) U.S. Cl.
CPC *G01L 1/241* (2013.01); *G01N 3/08* (2013.01); G01N 2203/0647 (2013.01); *G01B 11/162* (2013.01); G01N 2203/0286 (2013.01); *G01N 3/068* (2013.01)
USPC .............................................. 73/800; 73/777

(58) Field of Classification Search
CPC ................. G01B 11/161; G01L 1/241; G01N 2203/0286
USPC ....................................... 73/777, 800, 862.624
See application file for complete search history.

(56) References Cited

U.S. PATENT DOCUMENTS 4,869,110 A * 9/1989 Kent et al. ........................ 73/800
(Continued)

FOREIGN PATENT DOCUMENTS

JP 4-346004 1/1992
(Continued)

OTHER PUBLICATIONS

Takashi Ichinomiya, Massaaki Otsu, Kazuki Takashima, "Tensile Testing of Thin Films Using Laser Speckle Strain Measurement Technique" Dai 50 Kai Nippon Gakujutus Kaigi Zairyo Kogaku Rengo Koenkai Ronbunshu, Dec. 13, 2006, pp. 118-119.
International Search Report, dated Aug. 16, 2011; Issued on International Application No. PCT/JP2011/062565.

(Continued)

Primary Examiner — Max Noori
(74) Attorney, Agent, or Firm — Squire Patton Boggs (US) LLP

(57) ABSTRACT

A measurement unit for tensile or compressive stress can includes a CCD camera for detecting an interference light, the interference light being formed with a measurement beam from a measured region and a reference beam from a reference mirror. A first objective lens can have the reference mirror. An image processing apparatus can measure the three-dimensional shape of the measured region from the position of the first objective lens at which the interference light provides the maximum contrast and can measure the distance between two gauge points on the basis of the three-dimensional shape. When strain is generated on a micromaterial, the strain against the measured tensile stress is measured on the basis of the tensile stress and the distance between the two gauge points.

8 Claims, 7 Drawing Sheets

(56) References Cited

U.S. PATENT DOCUMENTS

| | | | |
|---|---|---|---|
| 5,757,473 A * | 5/1998 | Kanduth et al. | 356/32 |
| 5,923,637 A * | 7/1999 | Shimada et al. | 369/126 |
| 6,799,472 B2 * | 10/2004 | Nakayama et al. | 73/827 |
| 7,685,733 B2 * | 3/2010 | Ohmori et al. | 33/559 |
| 7,859,653 B2 * | 12/2010 | Ragucci et al. | 356/33 |

FOREIGN PATENT DOCUMENTS

| | | |
|---|---|---|
| JP | 8-313422 | 11/1996 |
| JP | 9-297009 | 11/1997 |
| JP | 2000-310518 | 11/2000 |
| JP | 2003-207432 | 7/2003 |
| JP | 2008-216021 | 9/2008 |

\* cited by examiner (A)

(B)

US 8,844,367 B2

MICROMATERIAL STRAIN MEASUREMENT APPARATUS AND METHOD THEREFOR

TECHNICAL FIELD

The present invention relates to a micromaterial strain measurement apparatus and a method therefor.

BACKGROUND ART

Recently, the semiconductor micromachining technology such as the photolithography technique, the thin film deposition technique, and the etching technique, which are performed mainly on silicon substrates, has been employed to manufacture a microstructure into which composite functions such as mechanical, electronic, optical, and chemical ones are integrated. The aforementioned microstructure is called a Micro Electro Mechanical Systems (MEMS) device, which is applied, for example, to actuators, pressure sensors, temperature sensors, acceleration sensors, and angular acceleration sensors. These MEMS devices have, as an essential elemental member, thin film of the order of submicrons to microns formed on a substrate. The thin film of the order of submicrons to microns may be different in material properties from bulk material, and thus the thin film material needs to be directly evaluated concerning the mechanical properties (such as the modulus of elasticity, strength, rupture toughness, and fatigue property). In this context, for evaluation of the mechanical properties, for example, a micromaterial strain measurement apparatus has been suggested as disclosed in Patent Literature 1.

Disclosed in Patent Literature 1 is that the deformation of micromaterial resulting from tensile stress or compressive stress is to be measured by a scanning probe microscope. More specifically, the micro deformation can be measured by providing the surface of the micromaterial with a minute grid line pattern serving as a gauge point and then measuring a change in the gauge point with the scanning probe microscope.

CITATION LIST

Patent Literatures

Patent literature 1: Japanese Patent Application Laid-Open No. 2003-207432

SUMMARY OF THE INVENTION

Problem to be Solved by the Invention

However, in Patent Literature 1, a gauge point is provided on the micromaterial. Thus, the surface of the micromaterial may be scratched when the gauge point is provided thereon, likely causing the micromaterial to be broken before being measured. Furthermore, the cantilever used in the scanning probe microscope makes a measurement substantially in contact with the micromaterial, making the positioning thereof difficult and thus requiring a well-organized measurement environment. Furthermore, as for the time required for measurement, since a region needs to be scanned point by point, the region is narrow, and it takes an enormous amount of time for measurement even when the region is a narrow one.

In order to avoid such situations, it was suggested to employ the distance between two chuck portions, which served to secure the micromaterial, as it was without providing any gauge point in order to determine the relation between tensile stress or compressive stress and the distance. Furthermore, it was also suggested that a gauge point to be provided would be drawn with paint or the like so as to minimize effects on the deformation of the micromaterial and not to cause any change in the property of the material. Then, the gauge point was photographed using a CCD camera or the like in order to measure the micromaterial in a noncontact fashion, and then strain was determined from the amount of displacement of the gauge point. However, in either case, it is thought to be difficult to accurately determine strain against tensile stress or compressive stress because the object to be measured is a micromaterial.

Further, such a method is also conceivable in which an irregular surface shape of the micromaterial may be irradiated with a laser beam so as to determine strain due to tensile stress or compressive stress from a change in the interference pattern (speckle pattern) of the scattered light of the laser beam. However, the speckle pattern is not directly representative of the surface shape but based on the feature of the irregular surface shape. Thus, the resolution required for the micromaterial is not always ensured. Furthermore, a change in the surface undulation of the micromaterial due to tensile stress or compressive stress would likely cause the speckle pattern employed as a gauge point in the initial state to be varied, or the speckle pattern employed as a gauge point in the initial state to disappear out of the field of view being observed. That is, it is thought to be difficult to accurately determine strain against tensile stress or compressive stress even using the speckle pattern because the object being measured is a micromaterial.

In this context, the present invention was developed in order to solve the aforementioned problems. It is therefore an object of the invention to provide a micromaterial strain measurement apparatus and a method therefor, which enable the strain of a micromaterial against tensile stress or compressive stress to be accurately measured even in a noncontact fashion.

Means for Solving the Problems

The present invention addresses the aforementioned problems by providing a micromaterial strain measurement apparatus, comprising: a strain generation unit for applying tensile stress or compressive stress to a micromaterial so as to generate strain on the micromaterial and measuring the tensile stress or compressive stress, and a measurement unit for measuring deformation of the micromaterial due to the strain, wherein: the measurement unit includes: a white light source for irradiating a measured region of the micromaterial; a two-dimensional photoelectric sensor for detecting interference light, the interference light being formed with a measurement beam of light from the measured region irradiated with the white light source and a reference beam of light from a reference mirror irradiated with light split from the white light source; a first objective lens which allows the two-dimensional photoelectric sensor to receive the interference light and includes the reference mirror; a second objective lens which has a constant positional relation with the first objective lens in an optical axis direction of the first objective lens, moved with the first objective lens, focal position of which is automatically adjusted from an image-forming state of the measured region on the two-dimensional photoelectric sensor, and replaceable with the first objective lens on the optical axis; and an image processing apparatus for measuring a three-dimensional shape of the measured region from a position of the first objective lens, at which the interference light provides the maximum contrast by relative scanning of the first objective lens in the optical axis direction and for defining a plurality of gauge points on the basis of the three-dimensional shape, the gauge points being reference positions for measuring a displacement of the measured region, the image processing apparatus further measuring a distance between the plurality of gauge points; the strain generation unit includes: two chuck portions for holding the micromaterial; stress detection means for supporting one of the two chuck portions and measuring the tensile stress or compressive stress; and a moving mechanism for generating the strain by changing the distance between the two chuck portions; and the position of the first objective lens is determined initially on the optical axis on the basis of the position of the second objective lens which has been automatically adjusted, when the moving mechanism generates the strain on the micromaterial, the strain against the tensile stress or compressive stress is measured on the basis of the tensile stress or compressive stress measured by the stress detection means and the distance between the plurality of gauge points which have been followed, identified, and measured without missing the plurality of gauge points varied due to the strain by relatively scanning the first objective lens from the position initially determined in the optical axis direction.

According to the present invention, the measurement unit includes a white light source, a two-dimensional photoelectric sensor for detecting interference light formed with a measurement beam and a reference beam, a first objective lens for allowing a two-dimensional photoelectric sensor to receive the interference light, and an image processing apparatus. Furthermore, the first objective lens is scanned across a micromaterial in the optical axis direction thereof. That is, the aforementioned constituent members constitute a scanning white light interferometer (to be discussed later). Thus, since the field of view (not a point but a plane) of the first objective lens can be measured at one time, the measured region can be measured in a shorter time than before. Furthermore, since the image processing apparatus measures the three-dimensional shape of the measured region from the position of the first objective lens at which the interference light provides the maximum contrast, the three-dimensional shape of the measured region can be quickly determined with high resolution. Thus, the deformation behavior of the measured region of the micromaterial at the micro level can be observed on the spot. At this time, since the micromaterial and the measurement unit are not in contact with each other, the micromaterial can be handled more easily than before. Furthermore, what is obtained by the white light interferometer is a direct three-dimensional shape of the measured region and thus, different from an interference pattern (speckle pattern) formed by scattered light based on the surface shape (the three-dimensional shape). That is, without drawing the gauge points on the micromaterial, the image processing apparatus of the white light interferometer can set a certain position on the surface shape of the measured region directly as the gauge points and measure the distance between the gauge points. Then, the white light interferometer measures the surface shape of the measured region including the certain position. Thus, when strain is generated on the micromaterial by the moving mechanism of the strain generation unit, even there is a change in the position of the gauge points including the height, the position can be continuously measured. That is, since the gauge points having been set can be followed and identified without being missed, the distance between the varying gauge points can be measured with stability. Even if the gauge points having been set under the initial conditions have gone out of the measured region, such a position that comes within the measured region can be set appropriately as the gauge points. At the same time, since the stress detection means of the strain generation unit measures the tensile stress or compressive stress which acts upon the micromaterial, the strain against the tensile stress or compressive stress can be measured accurately.

Thus, the present invention makes it possible to perform a strain measurement in conformity with the test method which was established in Japan Industrial Standard (JIS C5630-2, 3 established on Mar. 20, 2009) as the tensile testing method of thin film materials for MEMS devices.

Although nominal strain may be determined when determining strain from varying distance between the gauge points, the strain is preferably true strain which is determined from the distance between the plurality of gauge points in the absence of the strain and the distance between the plurality of gauge points in the presence of the strain. In that case, the strain can be determined with high accuracy not only for micro strain but also for a large deformation occurring in the measured region.

Two or more gauge points would enable it to determine the distance between the gauge points, but the plurality of gauge points may be three or more. In this case, a strain distribution can be determined in the measured region. Thus, since the strain distribution within the measured region can be evaluated in relation to the surface shape, the mechanical properties of the micromaterial can be grasped in greater detail.

The measurement unit includes a second objective lens which has a constant positional relation with the first objective lens in the optical axis direction of the first objective lens. The second objective lens is moved with the first objective lens. A focal position of the second objective lens is automatically adjusted from an image-forming state of the measured region on the two-dimensional photoelectric sensor. The second objective lens is replaceable with the first objective lens on the optical axis. According to the above, the focal positioning of the first objective lens on the measured region can quickly be performed. At the same time, the second objective lens can be used to observe the state of the measured region. Furthermore, even when the function of tilting the micromaterial relative to the optical axis direction is not available, the aforementioned function for automatically adjusting the focal position of the second objective lens makes it possible to measure the three-dimensional shape at reasonable speeds.

When the measurement unit further includes a laser processing unit which emits a laser beam capable of shaping the micromaterial, the micromaterial under shaping can be held in the strain generation unit, so that after the micromaterial is held, the micromaterial is processed into a final shape to be measured. This can prevent the concentration of mechanical stress on the measured region when being held, thereby effectively preventing the micromaterial from being broken when being held. Then, since the micromaterial is processed with a laser beam in a non-contact fashion, it is possible to minimize adverse effects on the measured region during the processing. As a result, it is possible to prevent the micromaterial from being damaged at the step of holding the micromaterial.

When one of the two chuck portions can be positioned relative to the other in mutually orthogonal three axis directions, the position of the chuck portions can be adjusted in the three axis directions when the micromaterial is held. Thus, since this allows stress acting upon the micromaterial when being held can be reduced as much as possible, the relation between strain and stress can be measured with improved accuracy and the micromaterial can be prevented from being broken when being held.

When the strain generation unit is also movable within a plane orthogonal to the optical axis direction and tiltable relative to the optical axis direction, the measured region of the micromaterial held in the strain generation unit can be quickly adjusted to the optical axis of the first objective lens. At the same time, the inclination of the measured region of the micromaterial can be reduced in advance (to be in a horizontal position). Thus, since the number of times of scanning the first objective lens in the optical axis direction can be reduced, the three-dimensional shape of the measured region can be measured at higher speeds. Furthermore, in measuring the three-dimensional shape of a measured region set to be broader than the field of view of the first objective lens, a synergistic effect with the function of automatically adjusting the focal position of the second objective lens allows all the surface shapes of the measured region to be continuously measured with good trackability.

The present invention can also be interpreted as a micromaterial strain measurement method to determine strain by applying tensile stress or compressive stress to a micromaterial so as to generate strain on the micromaterial, measuring the tensile stress or compressive stress, and measuring deformation of the micromaterial caused by the strain, the method including the steps of: holding the micromaterial; automatically adjusting a focal position of a second objective lens from an image-forming state of a measured region of the micromaterial by moving the second objective lens on an optical axis; replacing the second objective lens with a first objective lens which has a constant positional relation with the second objective lens, includes a reference mirror, and moves with the second objective lens in the optical axis direction; initially determining the position of the first objective lens on the basis of the position of the second objective lens on the optical axis; generating the strain on the micromaterial being held and measuring the tensile stress or compressive stress; irradiating the measured region of the micromaterial, to which the strain has been imparted, with light from a white light source; allowing a two-dimensional photoelectric sensor to receive interference light through the first objective lens including the reference mirror, the interference light being formed with a measurement beam of light from the measured region and a reference beam of light from the reference mirror irradiated with light split from the white light source; relatively scanning the first objective lens from the position initially determined in the optical axis direction thereof and measuring a three-dimensional shape of the measured region from a position of the first objective lens at which the interference light provides a maximum contrast; measuring a distance between a plurality of gauge points, on the basis of the measured three-dimensional shape, by following and identifying without missing a plurality of the gauge points, which serve as a reference position when measuring a displacement of the measured region changed due to the strain; and measuring the strain against the resulting tensile stress or compressive stress on the basis of the resulting distance between the plurality of the gauge points and the tensile stress or compressive stress.

When the micromaterial strain measurement method of the present invention includes a step of continuously applying the tensile stress or compressive stress to the micromaterial by deforming the micromaterial at a constant speed, it is possible to maintain a constant thermal equilibrium state caused by the deformation of the micromaterial if the constant speed is a certain strain speed. Thus, measurements can be performed with higher accuracy. Furthermore, even when tensile stress or compressive stress is different depending on the strain speed (distortion speed), the tensile stress or compressive stress can be determined with improved accuracy at a certain strain speed which is the constant speed.

Advantageous Effects of the Invention

The present invention makes it possible to measure strain against tensile stress or compressive stress with accuracy even in a noncontact fashion relative to a micromaterial.

MODE FOR CARRYING OUT THE INVENTION

Now, preferred embodiments for embodying the present invention will be described below in more detail with reference to the drawings.

Figure 1:
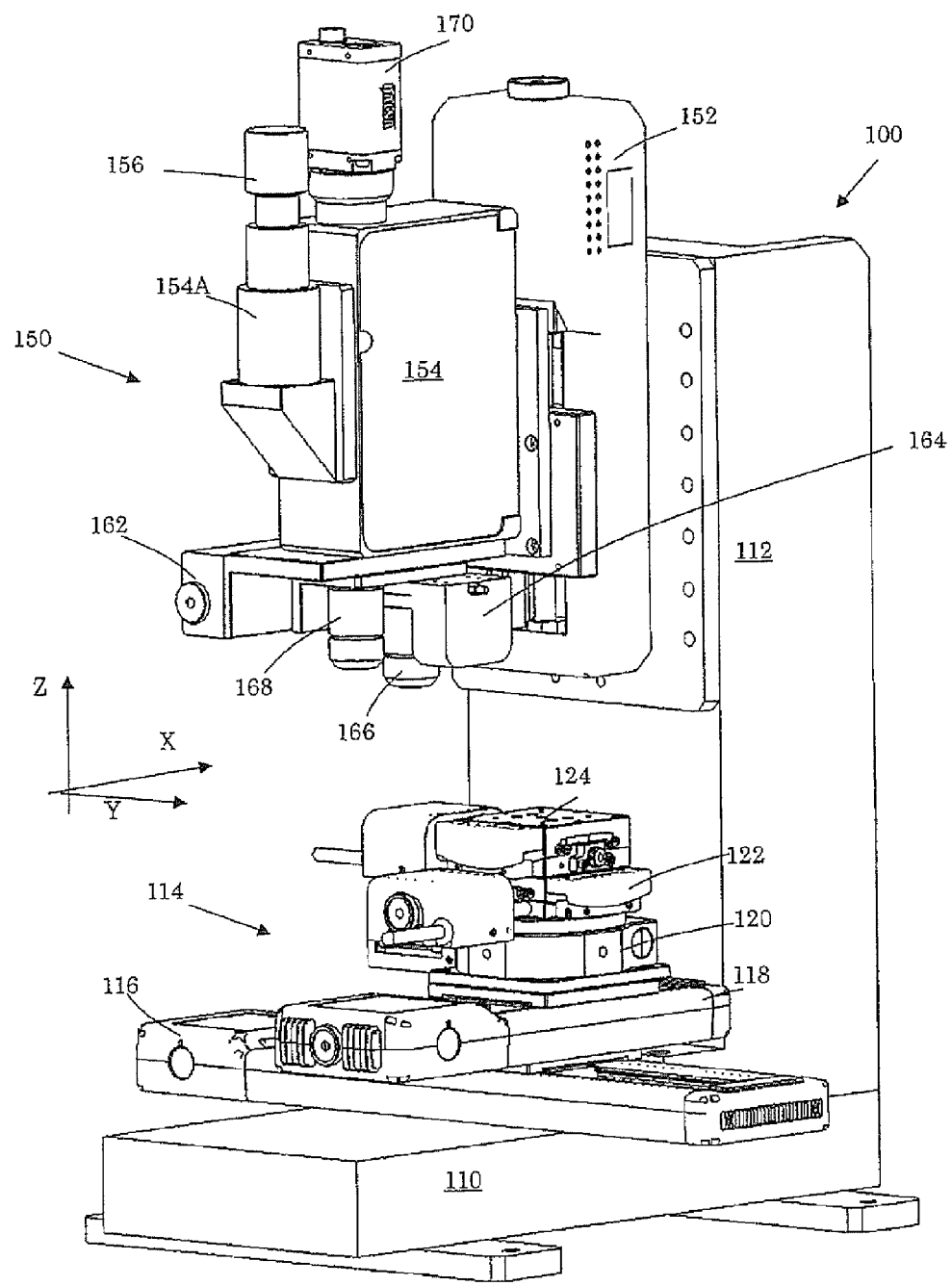
FIG. 1 is an overall perspective view illustrating a micromaterial strain measurement apparatus to which an example of an embodiment of the present invention is applied.
Figure 2:
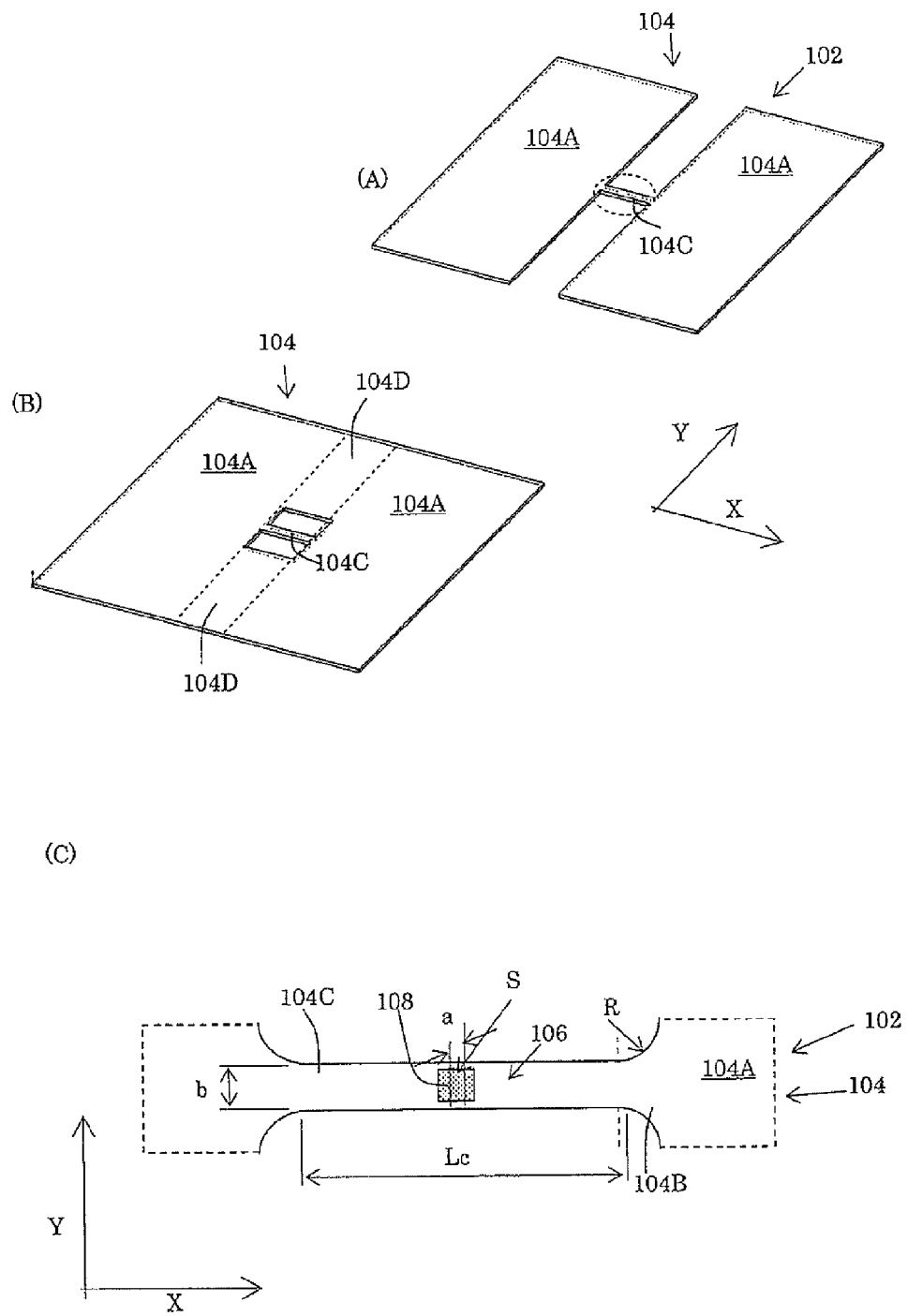
FIG. 2 shows perspective views (A) and (B) and an enlarged plan view (C) illustrating an example of a micromaterial.
Figure 3:
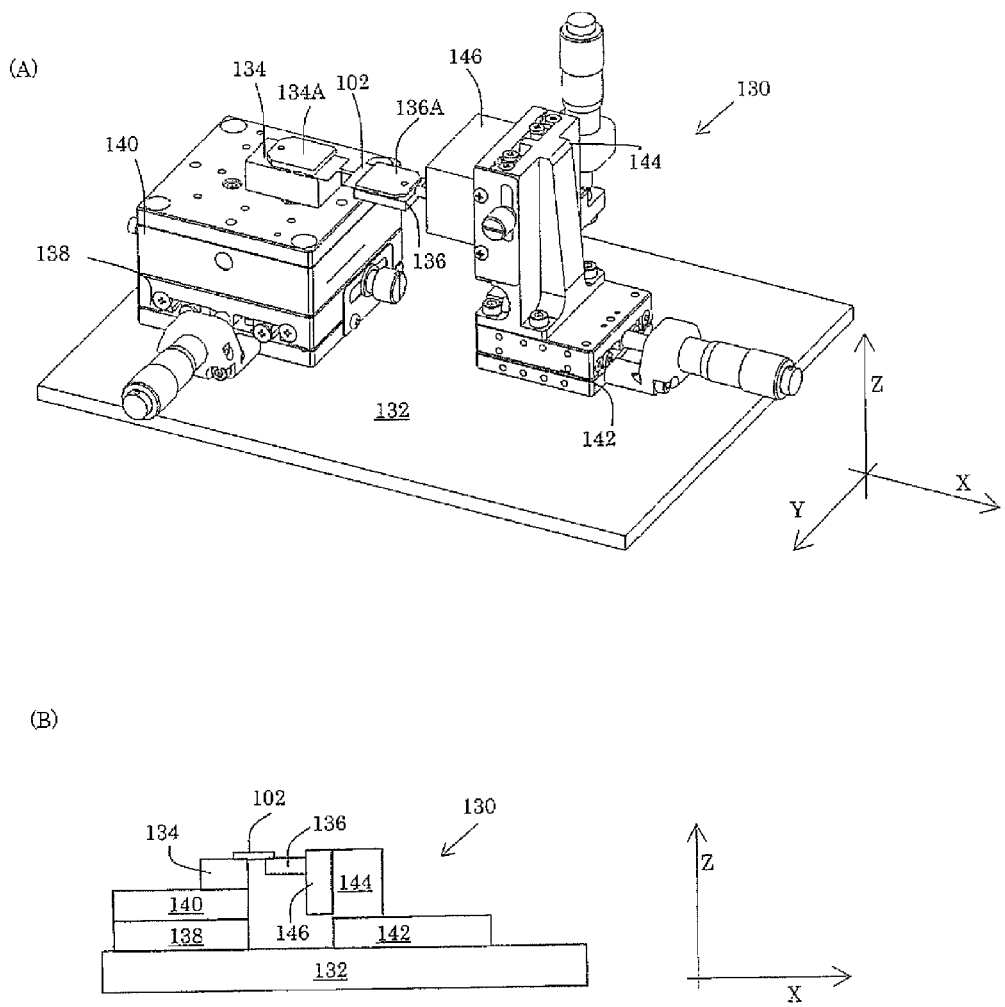
FIG. 3 shows a perspective view (A) and a side view (B), illustrating a strain generation unit for holding the micromaterial.

As shown in FIGS. 1 to 3, a micromaterial strain measurement apparatus 100 according to an embodiment of the present invention includes a positioning unit 114, a strain generation unit 130, and a measurement unit 150. The positioning unit 114 serves to position a measured region 108 of a micromaterial 102 and is secured onto a base plate 110. The strain generation unit 130 applies tensile stress or compressive stress to the micromaterial 102 so as to generate strain in the micromaterial 102 and measures tensile stress or compressive stress. The measurement unit 150 measures the deformation of the micromaterial 102 caused by strain.

Now, each component will be described in detail with reference to FIGS. 1 to 4. Note that descriptions will be made below only in relation to tensile stress.

As shown in FIG. 2(C) which is the broken line portion of FIG. 2(A), the micromaterial 102 is made up of a support base 104 and a thin film 106 deposited on the support base 104. The main portion of the micromaterial 102 shown in FIG. 2(C) is configured such that the length and width of a parallel portion 104C, to be discussed later, are specified to be equal to or less than 1 mm. Only the thin film 106 is to be measured. Thus, the result of a measurement of the thin film 106 is determined from the result of a measurement of the micromaterial 102 having the thin film 106 deposited on the support base 104 and from the result of a measurement of only the support base 104.

On both ends of the support base 104, there are provided grip portions 104A which are held by chuck portions 134 and 136 of the strain generation unit 130, to be discussed later. The parallel portion 104C is provided between the two grip portions 104A via a shoulder portion 104B which reduces the width of the grip portion 104A with a curvature R. The parallel portion 104C has a length Lc which is 2.5 times the width of the parallel portion 104C or greater. The parallel portion 104C can be provided, for example, at the center thereof with the measured region 108, as shown in FIG. 2(C). The measured region 108 is aligned with the field of view of a first objective lens 166, to be discussed later, and is a square about 100 μm per side. Note that the measured region may be configured to be greater than the field of view of the first objective lens 166, and have a width "b" in a Y direction and a length which is 80% or less the length Lc of the parallel portion 104C and twice the width "b" or greater in an extendable direction (in an X direction) (for example, the measured region may be made greater than the field of view of the first objective lens 166 and extended in the vicinity of the two shoulder portions 104B). In this case, two gauge points required by JIS as described above can be provided within the region to be measured. The thin film 106 is provided so as to cover at least the entire surface of the measured region 108. For example, the support base 104 is formed with silicon, while the thin film 106 is made of silicon film, silicon oxide film, or silicon nitride. Note that the gauge point is a reference position for the measurement of a displacement of the measured region 108. Furthermore, symbol "a" denotes the thickness of the thin film 106 and symbol S denotes the cross-sectional area of the parallel portion 104C of the thin film 106.

As shown in FIG. 1, the positioning unit 114 includes a Y stage 116, an X stage 118, a θ stage 120, a β stage 122, and an α stage 124. The Y stage 116 is secured onto the base plate 110 disposed on a vibration damping mechanism (not shown). The X stage 118 is orthogonal to the Y stage 116 and secured onto the Y stage 116. That is, the Y stage 116 and the X stage 118 can move the strain generation unit 130 secured to the α stage 124 within a plane orthogonal to the direction of an optical axis (the XY direction). The θ stage 120 has a rotation axis in the optical axis direction (Z direction) and is secured onto the X stage 118. The α stage 124 and the β stage 122 are gonio-stages which each tilt the surface thereof relative to the optical axis direction (Z direction). The β stage 122 is secured onto the θ stage 120, while the α stage 124 is secured onto the β stage 122 so as to be orthogonal to the tilted rotation axis of the β stage 122. Thus, the θ stage 120, the β stage 122, and the α stage 124 allow the strain generation unit 130 secured onto the α stage 124 to be freely tilted relative to the optical axis direction.

The strain generation unit 130 is secured onto the α stage 124. As shown in FIGS. 3(A) and (B), on a base plate 132, the strain generation unit 130 includes the two chuck portions 134 and 136, a Y stage 138, an inching X stage 140 (moving mechanism), an X stage 142, a Z stage 144, and a load cell 146. The Y stage 138 is secured onto the base plate 132, and the inching X stage 140 is secured onto the Y stage 138. Furthermore, the chuck portion 134 is provided on the inching X stage 140. The inching X stage 140 serves to apply tensile stress to the micromaterial 102 and employs a piezoelectric element (for example, PZT) as a driving source. Thus, the inching X stage 140 can be controlled, for example, with an accuracy of 10 nm. On the other hand, at a certain distance from the Y stage 138, the X stage 142 is secured onto the base plate 132 while the Z stage 144 is secured onto the X stage 142. The load cell 146 (stress detection means) is secured onto the surface of the Z stage 144 facing to the inching X stage 140, while the chuck portion 136 is provided on the load cell 146. The load cell 146, which is a strain gauge load cell, can detect (measure or gage) both dynamic stress and static stress. More specifically, for example, the load cell 146 has a detection resolution of 200 μN and can tolerate the maximum allowable load of about 2 N. In measuring a load, the load cell 146 ensures an accuracy higher than 5% the measurable load. The chuck portions 134 and 136 hold the grip portions 104A of the micromaterial 102. That is, the strain generation unit 130 includes the two chuck portions 134 and 136 for holding the micromaterial 102, with one chuck portion 134 (136) capable of being positioned relative to the other 136 (134) in the mutually orthogonal three axial directions. Note that the two chuck portions 134 and 136 are provided with flat-shaped retainer members 134A and 136A for retaining the grip portions 104A of the micromaterial 102 from the upper surfaces, respectively.

As shown in FIG. 1, the measurement unit 150 is secured onto a bracket 112 which stands erectly on the base plate 110. The measurement unit 150 has a Z stage 152, a lens barrel 154, a white light source 156, a slider 162, an inching Z stage 164, the first objective lens 166, a second objective lens 168, and a CCD camera 170 (a two-dimensional photoelectric sensor).

The Z stage 152 is secured onto the bracket 112 and provided with the lens barrel 154 secured to a movable portion thereof. In the present embodiment, the Z stage 152 has a stroke of 50 mm. The lens barrel 154 is provided with an epi-illumination unit 154A, on top of which mounted is the white light source 156. The white light source 156 is employed to irradiate the measured region 108 of the micromaterial 102. The white light source 156 is a white LED, but may also be one which has a spread in spectrum to some extent, such as a halogen lamp, xenon lamp, mercury lamp, metal halide lamp, or super luminescent diode (SLD).

Figure 4:
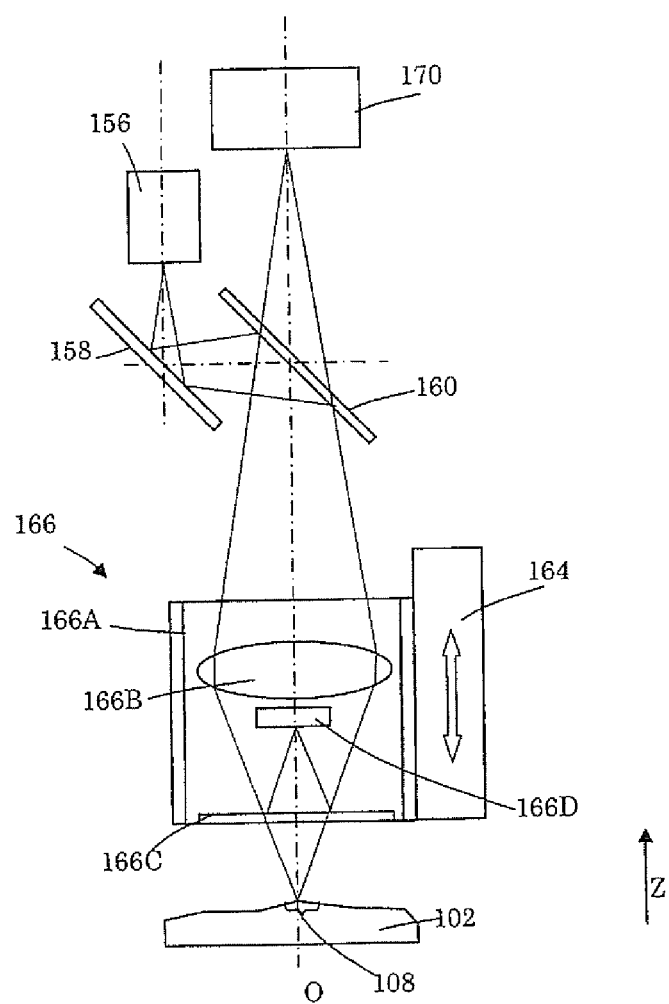
FIG. 4 is a schematic view illustrating a general configuration of a white light interferometer in a measurement unit.

As shown in FIG. 4, the lens barrel 154 is provided therein with a reflective mirror 158 and a half mirror 160. The reflective mirror 158 and the half mirror 160 can direct a beam of light emitted from the white light source 156 in an optical axis O.

The first objective lens 166 and the second objective lens 168 are provided on the lower portion of the lens barrel 154 facing to the strain generation unit 130 via the slider 162. The slider 162 moves the first objective lens 166 and the second objective lens 168 in the Y direction, thereby allowing the first objective lens 166 and the second objective lens 168 to be interchangeable with each other on the optical axis O shown in FIG. 4 with no change in position in the optical axis direction (Z direction). That is, the first objective lens 166 and the second objective lens 168 provide a constant positional relation in the optical axis direction. The first objective lens 166 and the second objective lens 168 have the same focal position in the optical axis direction (Z direction). The second objective lens 168 is combined with the Z stage 152 so that the focal position of the second objective lens 168 is automatically adjusted from the image-forming status of the measured region 108 on the CCD camera 170, to be discussed later. Thus, with the focal position of the second objective lens 168 automatically adjusted, the focal positioning of the first objective lens 166 is completed only by replacing the second objective lens 168 with the first objective lens 166 by the slider 162.

The inching Z stage 164 is disposed between the first objective lens 166 and the slider 162. The inching Z stage 164 can scan the first objective lens 166 in the optical axis direction (Z direction). The inching Z stage 164 can be controlled with a resolution of 0.1 nm using a piezoelectric element (for example, PZT) as a driving source. As shown in FIG. 4, the first objective lens 166 has a lens 166B, a half mirror 166C, and a reference mirror 166D inside the holder 166A, thus forming a Mirau-type interference optical system. The half mirror 166C and the reference mirror 166D are disposed on the optical axis O. That is, the half mirror 166C splits a beam of light transmitted from the lens 166B. Then, the reference mirror 166D reflects the split light to form a reference beam. On the other hand, a beam of light from the measured region 108 having passed through the half mirror 166C forms a measurement beam. The second objective lens 168 is used to observe the measured region 108 and initially determine the focal position of the first objective lens 166. Note that in the present embodiment, the first objective lens 166 and the second objective lens 168 are 50-powered and 20-powered lenses, respectively. Thus, in relation to the size of one pixel of the CCD camera 170, the first objective lens 166 is designed to have a submicron horizontal resolution.

The lens barrel 154 is provided on the upper portion with the CCD camera 170. The CCD camera 170 is a two-dimensional photoelectric sensor for receiving light from the first objective lens 166 or the second objective lens 168. That is, the white light source 156 and the first objective lens 166 form an interference light on the light receiving surface of the CCD camera 170. That is, the measurement unit 150 employs the inching Z stage 164, thereby forming a scanning white light interferometer. Now, a description will be made to the principle of the white light interferometer with reference to FIG. 4.

Light emitted from the white light source 156 passes through the epi-illumination unit 154A of the lens barrel 154 and is then aligned with the optical axis O by the reflective mirror 158 and the half mirror 160 so as to be incident upon the first objective lens 166. The light transmitted from the lens 166B of the first objective lens 166 is split by the half mirror 166C in a holder 166A. The light that has not been split is transmitted through the half mirror 166C and then irradiates the measured region 108. The light scattered from the measured region 108 (the measurement beam of light from the measured region 108 irradiated with the white light source 156) is incident again upon the half mirror 166C of the first objective lens 166. On the other hand, the light split by the half mirror 166C is reflected on the reference mirror 166D in the holder 166 and then reflected again on the half mirror 166C (the reference beam of light from the reference mirror 166C irradiated with the light split from the white light source 156). At the same time, the measurement beam and the reference beam are superimposed at the half mirror 166C and then focused by the lens 166B on the light receiving surface of the CCD camera 170, forming a two-dimensional interference pattern (interference light) (allowing the CCD camera 170 to receive the interference light through the first objective lens 166). The two-dimensional interference pattern occurs due to the difference between the optical paths of the measurement beam and the reference beam. Since the white light source 156 has a certain spectrum width, it's coherency is low (a coherence length is short). Thus, the two-dimensional interference pattern appears in a very narrow range in the optical axis direction, so that an interference image (a light and dark pattern) of the maximum contrast can be obtained at the position at which the optical path lengths coincide with each other. That is, in order to make each pixel of the CCD camera 170 have the maximum contrast, the first objective lens 166 is scanned relatively across the micromaterial 102 in the optical axis direction. This makes it possible to determine the height of the measured region 108 in the Z direction from the output of the CCD camera 170, i.e., the position of the first objective lens 166 in the optical axis direction (the Z direction) at which the interference image (interference light) provides the maximum contrast (the measurement of a three-dimensional shape). The first objective lens 166 is scanned by the inching Z stage 164. Note that the white light allows an interference pattern to appear in a narrower range as compared with a single spectrum beam of light, thus making it possible to measure the three-dimensional shape of the measured region 108 at a higher resolution.

The CCD camera 170 is connected with an image processing apparatus (not shown). The image processing apparatus can determine the height in the Z direction at each pixel of the CCD camera 170 by means of a position signal from the inching Z stage 164. This makes it possible to measure the aforementioned three-dimensional shape of the measured region 108 by the image processing apparatus. Furthermore, the image processing apparatus defines two gauge points in the measured region 108 on the basis of the resulting three-dimensional shape of the measured region 108, so as to measure the distance between the two gauge points each time the distance between the chuck portions 134 and 136 changes. In the present embodiment, in determining the three-dimensional shape of the measured region 108 with no strain, the two gauge points were defined in the X direction within the measured region 108 so as to be located at the two positions of maximum heights in the Z direction across the minimum height in the Z direction. This ensures the measurement (gaging) of a strain value which is 0.1% or less. Furthermore, the image processing apparatus can determine the relation between the true strain ϵt and the stress σ, which will be shown below, and then output the result on a monitor (not shown). Note that the monitor can display the two-dimensional interference pattern provided by the first objective lens 166, a measured three-dimensional shape image, and a pictorial image of the measured region 108 observed by the second objective lens 168.

The true strain ϵt can be determined by Equation (1) below from the distance between the two gauge points as:

$$\epsilon t = \ln(L1/L0) \quad (1)$$

where symbol L0 is the initial distance between the gauge points in the absence of strain, and symbol L1 is the distance between the gauge points in the presence of strain applied.

Furthermore, the stress σ can be determined by Equation (2) below as:

$$\sigma = Ld/S \quad (2)$$

where S is the cross-sectional area of the thin film 106 in the measured region 108 (=(the width "b" of the parallel portion)×(the thickness "a" of the thin film)), and Ld is the tensile stress applied between the chuck portions 134 and 136.

Here, to determine the nominal stress σf, the initial cross-sectional area with no strain may be employed as the cross-sectional area S, whereas to determine the true stress σt, a cross-sectional area which varies each time the thin film 106 is distorted may be employed as the cross-sectional area S.

Although not illustrated, the lens barrel 154 of the measurement unit 150 includes a laser processing unit which emits a laser beam which can shape the micromaterial 102. This allows the micromaterial 102 held in the strain generation unit 130 on top of the α stage 124 to be moved onto the optical axis of the laser processing unit by positioning the Y stage 116 and the X stage 118. In the laser processing unit, the micromaterial 102 under shaping is irradiated with a laser beam, thereby shaping the final micromaterial 102 which is to be measured.

Figure 5:
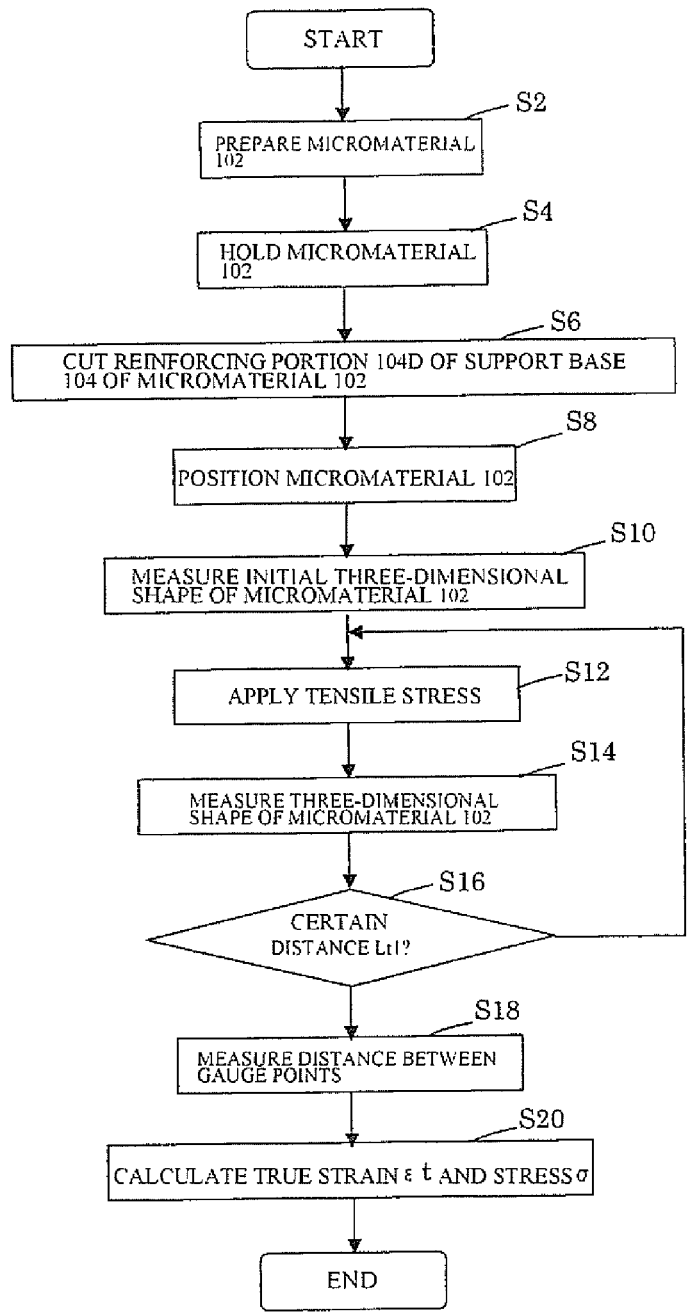
FIG. 5 is a flowchart of the measurement steps of a micromaterial strain measurement method.

Now, referring to FIG. 5, a description will be made to the micromaterial strain measurement method for measuring strain by the micromaterial strain measurement apparatus 100 of this embodiment, starting with the step of preparing the micromaterial 102.

First, the micromaterial 102 is prepared (Step S2). More specifically, as shown in FIG. 2(B), the parallel portion 104C of the support base 104 which supports the thin film 106 is formed. At this time, to avoid the concentration of stress on the shoulder portions 104B, the radius of the curvature R thereof is sufficiently increased and the shoulder portions 104B are formed to be as smooth as possible. In addition, the support base 104 is formed to have a reinforcing portion 104D left. Then, the entire support base 104 is placed on an apparatus for forming the thin film 106 to be measured, forming the thickness "a" to be measured. Note that the thickness "a" is measured at the time of forming the thin film, within an accuracy of 5%.

Next, the micromaterial 102 is held (Step S4). More specifically, the support base 104 of FIG. 2(B) with the thin film 106 formed thereon is secured to the chuck portions 134 and 136 of the strain generation unit 130 shown in FIGS. 3(A) and (B). The Y stage 138, the X stage 142, and the Z stage 144 are adjusted so that the two chuck portions 134 and 136 come to the positions of the two grip portions 104A of the micromaterial 102. Then, the micromaterial 102 is disposed on the chuck portions 134 and 136 with the retainer members 134A and 136A removed. Then, the grip portions 104A are temporarily retained with the retainer members 134A and 136A. At this time, fine adjustments are made to the Y stage 138, the X stage 142, and the Z stage 144 so that the load detected on the load cell 146 is zero. That is, one chuck portion 134 (136) is adjusted relative to the other 136 (134) in the mutually orthogonal three axis directions. When the load becomes zero, the grip portions 104A are securely fixed with the retainer members 134A and 136A, and at the same time, the Y stage 138, the X stage 142, and the Z stage 144 are fixed in that condition. Note that in the present embodiment, the retainer members 134A and 136A are screwed to the chuck portions 134 and 136, so that the amount of screwing can control the force acting upon the grip portions 104A.

Then, the reinforcing portion 104D of the support base 104 of the micromaterial 102 is cut (Step S6). More specifically, the reinforcing portion 104D of the micromaterial 102 is moved by the Y stage 116 and the X stage 118 to the optical axis of the laser processing unit in the measurement unit 150 in order to cut the reinforcing portion 104D with a laser beam. That is, the micromaterial 102 under shaping is irradiated with the laser beam, thereby forming the micromaterial 102 into the final shape to be measured as shown in FIG. 2(A). Thus, the presence of the reinforcing portion 104D can serve to protect the micromaterial 102 from breakage when the micromaterial 102 is held, and the measured region 108 can be measured with high accuracy in the step of measuring the micromaterial 102.

Now, the micromaterial 102 is positioned (Step S8). More specifically, the positioning unit 114 shown in FIG. 1 is used to move the strain generation unit 130 into place. That is, the measured region 108 of the micromaterial 102 held in the strain generation unit 130 is moved within a plane orthogonal to the optical axis O, and then, the measured region 108 is moved to the optical axis O by using the Y stage 116 and the X stage 118. Then, the θ stage 120, the β stage 122, and the α stage 124 are used to adjust the horizontality of the thin film 106 of the micromaterial 102. That is, the micromaterial 102 is tilted relative to the optical axis direction. Then, the measured region 108 of the micromaterial 102 being held is irradiated with light from the white light source 156. Then, using the Z stage 152, the focal position of the second objective lens 168 is automatically adjusted from the image-forming state of the measured region 108 on the CCD camera 170. Then, the measured region 108 is observed through the second objective lens 168 so as to position the measured region 108 by means of the Y stage 116 and the X stage 118. Then, the slider 162 is operated to place the first objective lens 166 on the optical axis O. At this time, the surface of the measured region 108 comes into the focal position of the first objective lens 166.

Figure 6:
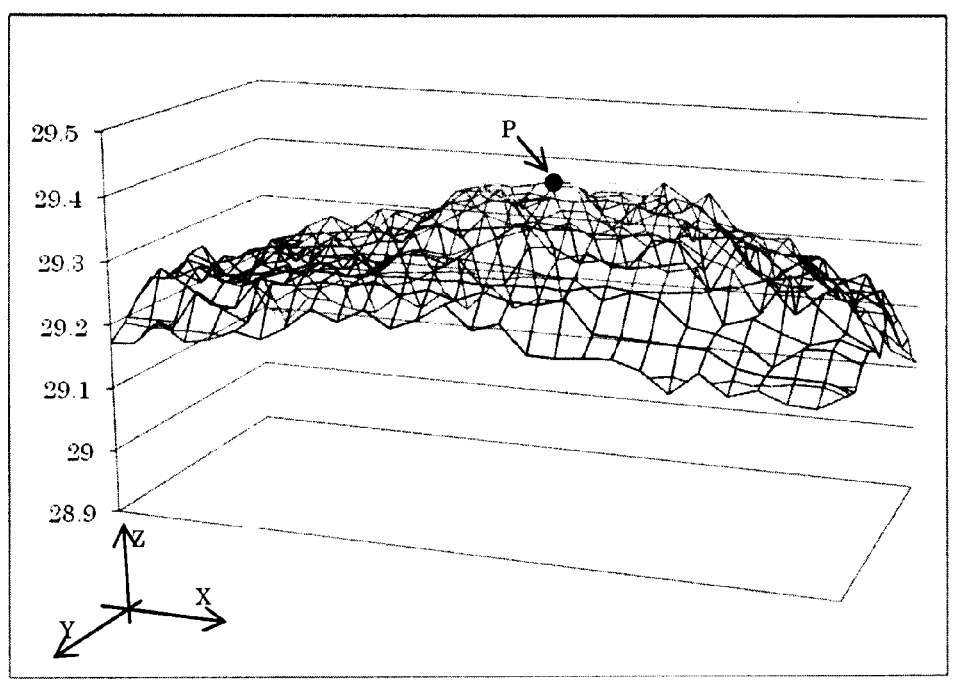
FIG. 6 shows a bird's eye view (A) and a contour map (B) in a Z direction, which illustrate an example of the three-dimensional shape of a measured region.
Figure 6:
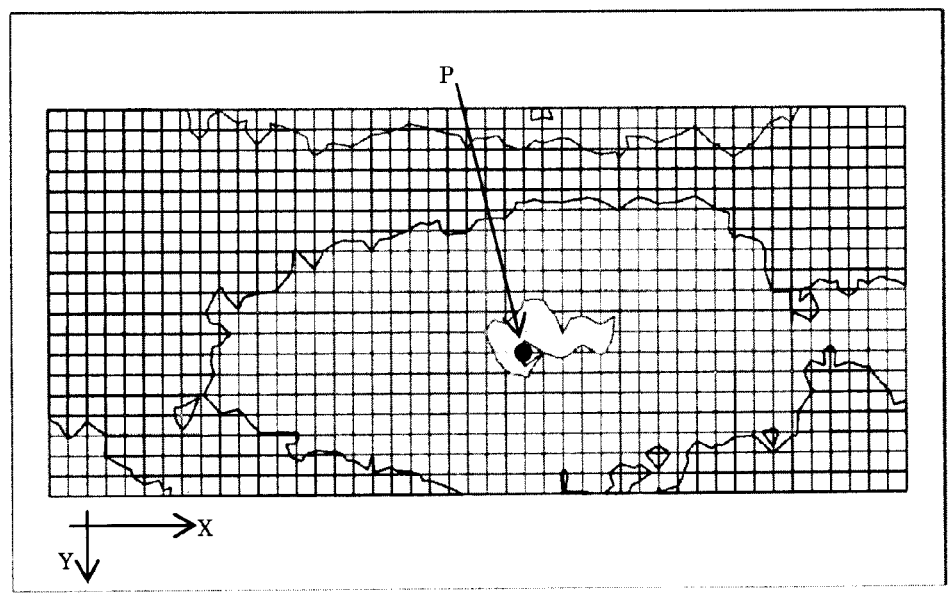

Then, the three-dimensional shape of the micromaterial 102 is measured. More specifically, the measurement beam from the measured region 108 and the reference beam from the reference mirror 166D irradiated with the light split from the white light source 156 form the interference light, which is received on the CCD camera 170 through the first objective lens 166. Then, using the inching Z stage 164, the first objective lens 166 is scanned relatively across the micromaterial 102 in the optical axis direction. Then, the position in the Z direction is determined at which the maximum contrast by white light interference is available for each pixel of the CCD camera 170, thereby measuring the three-dimensional shape of the measured region 108 from the output of the CCD camera 170, that is, from the position of the first objective lens 166 at which the interference light provides the maximum contrast. The three-dimensional shape of the measured region 108 can be determined as a numerical value indicative of the height of the measured region 108 in the Z direction at each pixel of the CCD camera 170. That is, each of the numerical values are obtained in a matrix assuming the field of view of the CCD camera 170, thereby determining the three-dimensional shape of the measured region 108. Note that to visually identify the three-dimensional shape, a spreadsheet program or the like is used to provide color coded display, contour map display (FIG. 6(B)), or bird's eye view display (FIG. 6(A)) according to the magnitude of the numerical values. This allows for easily grasping the three-dimensional shape of the measured region 108. Thus, the gauge points, to be discussed later, can be readily defined, and even a change in the gauge points could be easily followed and identified.

Then, on the basis of the measured three-dimensional shape, the horizontality of the measured region 108 of the micromaterial 102 is adjusted using the θ stage 120, the β stage 122, and the α stage 124 so that the surface of the micromaterial 102 is horizontal on average. Until the certain horizontality corresponding to the measurement accuracy or the like is achieved, the measurement of the three-dimensional shape of the micromaterial 102 and the adjustment of the horizontality of the micromaterial 102 are repeated as required. In this manner, the micromaterial 102 can be placed with accuracy, thereby providing improved reliability to the strain measurement itself as compared with conventional manners.

Next, the initial three-dimensional shape of the micromaterial 102 is measured prior to being distorted (Step S10). Note that the three-dimensional shape is measured as described above. At this time, the width "b" of the parallel portion 104C of the micromaterial 102 is also measured. Note that this step may also be performed as part of the step of positioning the micromaterial 102.

Next, a certain (for example, several hundred nm to a few μm) displacement is imparted between the chuck portions 134 and 136, thereby allowing tensile stress to act upon the micromaterial 102 (Step S12). That is, strain is generated on the micromaterial 102 being held, and the tensile stress is measured. Then, this is temporarily stopped. At this time, the pulling is desirably performed at a strain speed of 0.01/second or less.

Next, the three-dimensional shape of the measured region 108 of the micromaterial 102 is measured (Step S14). Note that the three-dimensional shape is measured as described above. After the three-dimensional shape has been measured, a certain displacement is imparted again between the chuck portions 134 and 136, thereby applying tensile stress to the micromaterial 102 (Step S12). This is performed until the distance between the chuck portions 134 and 136 becomes a certain distance Ltl. For example, the measurement may be repeated a few tens of times.

Next, when the distance between the chuck portions 134 and 136 has reached the certain distance Ltl, the chuck portions 134 and 136 are stopped moving. Then, from the three-dimensional shape obtained for each displacement by a certain amount, two positions within the measured region 108 are defined as gauge points and the gauge points being varied due to the strain are not missed but followed and identified in order to measure the distance between the gauge points each time (Step S18). The gauge point P is determined to have the maximum value (or may have the minimum value) of the numerical values indicative of the three-dimensional shape of a specific region noted in the measured region 108 (a region in FIGS. 6(A) and (B)). Here, the specific regions are respectively defined as being closest to each of the two shoulder portions 104B of the measured region 108. Also, the specific region is aligned with the field of view of the first objective lens 166. Thus, the entire three-dimensional shape of the specific region obtained for each displacement by a certain amount between the chuck portions 134 and 136 can be grasped. That is, even when the position and value of the gauge points are changed, the position of the gauge points can be easily followed irrespective of the change.

Next, from the distance between the gauge points, the true strain $\epsilon t$ and the stress $\sigma$ are calculated based on Equations (1) and (2) (Step S20). At that time, an increase in strain is determined from the distance Li between the gauge points at the number of times of measurements "i" and the distance "Li+1" between the gauge points at the number of times of measurements "i+1," and then all the increases in strain are added up to determine the true strain $\epsilon t$ (an increase in strain for the true strain $\epsilon t$ is determined by replacing the distance L0 and the distance L1 by the distance Li and the distance "Li+1" in Equation (1), respectively).

Figure 7:
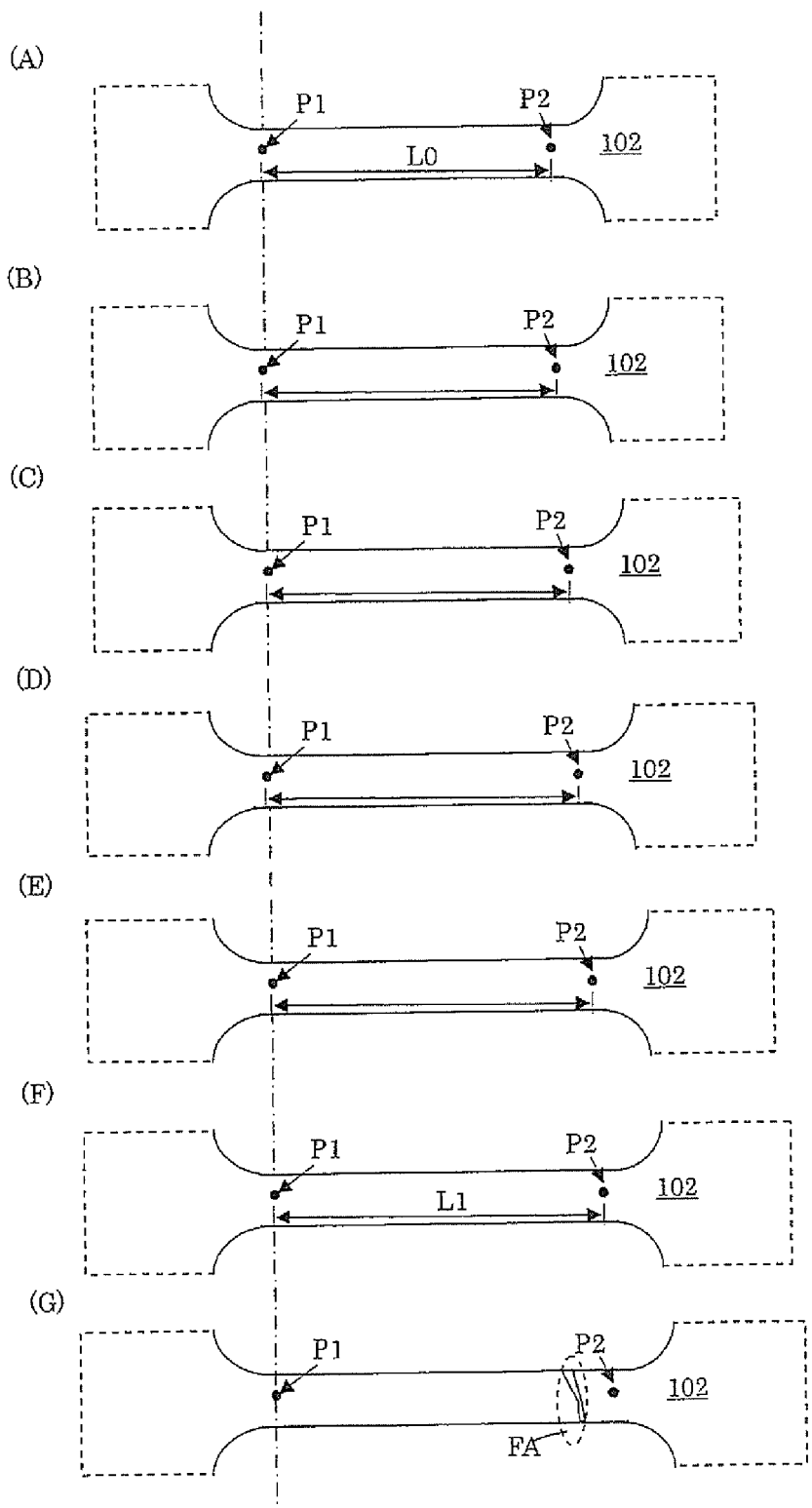
FIG. 7 is a schematic diagram illustrating an example of a change in gauge points when the distance between chuck portions is varied by a certain displacement.

FIG. 7 shows the strain-free (the absence of the strain) initial state with the gauge points P1 and P2 provided respectively in the vicinity (specific region) of the two shoulder portions 104B of the micro region 102 (FIG. 7(A) with the distance L0 between the gauge points), and each of changes in the gauge points P1 and P2 with strain having been imparted by a certain amount of displacement (FIGS. 7(B) to 7(G)). Note that in FIG. 7(G), the micromaterial 102 is ruptured between the gauge points P1 and P2 (a ruptured region FA encircled with a broken line). Thus, the true strain $\epsilon t$ can be determined up to FIG. 7(F) immediately before FIG. 7(G). Thus, even when the position recognized as the gauge points has gone out of the measured region 108 at the final number of times of measurements n, the true strain $\epsilon t$ can be determined from the increase in strain before then. That is, the true strain $\epsilon t$ can be determined with stability. The relation between the resulting true strain $\epsilon t$ and the stress $\sigma$ is output on the monitor or the like. Note that in the present embodiment, the target to be measured is the thin film 106 of the micromaterial 102. Thus, the aforementioned series of strain measurements is performed on the support base 104 only, and the support base 104 with the thin film 106. Then, from the two evaluation results, the relation between the true strain $\epsilon t$ and the stress $\sigma$ is determined only for the thin film 106.

In the present embodiment, the measurement unit 150 includes the white light source 156, the first objective lens 166, the CCD camera 170, and the image processing apparatus. Further, the first objective lens 166 is scanned relatively across the micromaterial 102 in the optical axis direction (in the Z direction). That is, the aforementioned constituent members constitute the scanning white light interferometer. Since the field of view (not a point but a plane) of the first objective lens 166 can be measured at one time, the measured region 108 can be measured in a shorter time than before. Furthermore, since the image processing apparatus measures the three-dimensional shape of the measured region 108 from the position of the first objective lens 166 at which the interference light provides the maximum contrast, the three-dimensional shape of the micromaterial 102 can be quickly determined with high resolution. Thus, the deformation behavior of the measured region 108 of the micromaterial 102 at the micro level can be observed on the spot. At this time, since the micromaterial 102 and the measurement unit 150 are not in contact with each other, the micromaterial 102 can be handled more easily than before. Furthermore, what is obtained by the white light interferometer is a direct three-dimensional shape of the measured region 108 and thus, different from an interference pattern (a speckle pattern) formed by scattered light based on the surface shape (the three-dimensional shape). That is, without drawing the gauge points on the micromaterial 102, the image processing apparatus of the white light interferometer can set a certain position on the surface shape of the measured region 108 directly as the gauge points and measure the distance between the gauge points. Then, the white light interferometer measures the surface shape of the measured region 108 including the certain position. Thus, when strain is generated on the micromaterial 102 by the inching X stage 140 of the strain generation unit 130, even there is a change in the position of the gauge points including the height, the position can be continuously measured. That is, since the gauge points having been set can be followed and identified without being missed, the distance between the varying gauge points can be measured with stability. Even if the gauge points having been set under the initial conditions have gone out of the measured region, such a position that comes within the measured region can be set appropriately as the gauge points. At the same time, since the load cell 146 of the strain generation unit 130 measures the tensile stress which acts upon the micromaterial 102, the strain against the tensile stress can be measured accurately.

Thus, this embodiment makes it possible to perform a strain measurement in conformity with the test method which was established in Japan Industrial Standard (JIS C5630-2, 3 established on Mar. 20, 2009) as the tensile testing method of thin film materials for MEMS devices.

Furthermore, strain $\epsilon$ is employed as the true strain $\epsilon t$ which is determined from the distance L0 between the two gauge points in the absence of the strain $\epsilon$ (initial condition) and the distance L1 between the two gauge points in the presence of the strain $\epsilon$. Thus, strain $\epsilon$ can be determined with high accuracy not only when the strain $\epsilon$ is micro strain but also when the measured region 108 is greatly deformed.

Furthermore, the measurement unit 150 further includes the second objective lens 168 which is disposed at the same focal position as that of the first objective lens 166 in the optical axis direction (the positional relation is constant). The focal position of the second objective lens 168 is automatically adjusted from the image-forming state of the measured region 108 on the CCD camera 170. Thus, the focal positioning of the first objective lens 166 on the measured region 108 can be performed very quickly. At the same time, the second objective lens 168 can be used to observe the state of the measured region 108. Furthermore, even when the function of tilting the micromaterial 102 relative to the optical axis direction is not available or not sufficient, the function for automatically adjusting the focal position of the second objective lens 168 makes it possible to measure the three-dimensional shape with reasonable accuracy.

Furthermore, the measurement unit 150 further includes the laser processing unit which emits a laser beam capable of shaping the micromaterial 102. Thus, the micromaterial 102 under shaping can be held by the chuck portions 134 and 136, so that after the micromaterial 102 is held, the micromaterial 102 is processed into the final shape to be measured. That is, the reinforcing portion 104D can be made available so as to effectively prevent the concentration of mechanical stress on the measured region 108 when the micromaterial 102 is held, and the reinforcing portion 104D can be cut after the micromaterial 102 is held. It is thus possible to effectively prevent the micromaterial 102 from being broken when being held. Furthermore, since the micromaterial 102 is processed with a laser beam in a non-contact fashion, it is possible to minimize adverse effects on the measured region 108 during the processing. As a result, it is possible to prevent the micromaterial 102 from being damaged at the step of holding the micromaterial 102.

Furthermore, one chuck portion 134 (136) of the two chuck portions 134 and 136 can be positioned relative to the other 136 (134) in the mutually orthogonal three axis directions. Thus, when the micromaterial 102 is held, the positions of the chuck portions 134 and 136 can be adjusted in the three axis directions. That is, since stress acting upon the micromaterial 102 when being held can be reduced as much as possible, the relation between strain and stress can be measured with improved accuracy and the micromaterial 102 can be prevented from being broken when being held.

Furthermore, the strain generation unit 130 is also movable within a plane orthogonal to the optical axis direction and tiltable relative to the optical axis direction. Thus, the measured region 108 of the micromaterial 102 held in the strain generation unit 130 can be quickly adjusted to the optical axis of the first objective lens 166. At the same time, the inclination of the measured region 108 of the micromaterial 102 can be reduced in advance (to be in a horizontal position). Thus, the number of times of scanning the first objective lens 166 in the optical axis direction can be reduced. Thus, the three-dimensional shape of the measured region 108 can be measured at higher speeds. Note that in measuring the three-dimensional shape of a measured region set to be broader than the field of view of the first objective lens 166, the combination of the Y stage 116 and the X stage 118 and the function of automatically adjusting the focal position of the second objective lens 168 create a synergistic effect, which allows all the surface shapes of the measured region to be continuously measured with good trackability.

Furthermore, in the present embodiment, a certain displacement is imparted between the chuck portions 134 and 136 to apply tensile stress to the micromaterial 102, and then after a temporary halt, the three-dimensional shape is measured. With this configuration, since the distance between the gauge points can be determined with reliability for each displacement by a certain amount, the aforementioned certain amount of displacement can be set in finer increments, thereby allowing the relation between the true strain and the stress to be determined in greater detail.

That is, according to this embodiment, the strain against the tensile stress can be accurately measured even in a non-contact fashion relative to the micromaterial 102.

The present invention has been described in accordance with the present embodiment. However, the present invention is not limited to this embodiment. That is, it is needless to say that improvements and design modifications may be made without departing from the scope of the present invention.

In the present embodiment, although a description was made in relation to tensile stress, the present invention is not limited only to tensile stress. The present invention can also be applied in the same manner to strain resulting from compressive stress or shear stress under the same technical concept only by changing the direction of stress.

Furthermore, although in the present embodiment, the single thin film 106 is to be measured and evaluated in conjunction with the support base 104, the present invention is not limited thereto. For example, thin film may also be independently located only on the measured region. In this case, strain can be measured with higher accuracy. Furthermore, thin film may also have a multi-layered film structure. In that case, by determining a two-dimensional strain distribution, a strain distribution can be determined, for example, in the vicinity of a singular structure caused by the multi-layered film structure (such as a layered structure or a structure containing a precipitate). That is, since a distribution can be determined for a thin film having a multi-layered film structure, new process suggestions and improvements or yield improvements can be made in applying the multi-layered film structure to MEMS.

Furthermore, in the present embodiment, the distance between the gauge points is determined each time the three-dimensional shape is measured so as to determine the true strain $\epsilon t$. However, the present invention is not limited thereto. For example, the true strain $\epsilon t$ may be determined using Equation (1) from the first distance L0 between the gauge points and the nth distance Ln (=L1) finally obtained between the gauge points (corresponding to the case where only the distance between the gauge points as shown in FIG. 7(A) and FIG. 7(F) is employed). In that case, since the cumulative error up to the nth one is reduced, the true strain $\epsilon t$ can be determined with less error.

Furthermore, in the present embodiment, the strain $\epsilon$ is employed as the true strain $\epsilon t$ which is determined by Equation (1). However, the present invention is not limited thereto but may also employ nominal strain $\epsilon f$. The nominal strain $\epsilon f$ can be determined as shown in Equation (3) below:

$$\epsilon f = (L1-L0)/L0 \tag{3}$$

where symbol L0 denotes the initial distance between the gauge points under no strain and symbol L1 denotes the distance between the gauge points after strain has been imparted. The nominal strain $\epsilon f$ can be determined at higher speeds with a less amount of computation. In the case of a micro strain region, the relation between stress and strain can be determined with accuracy.

Furthermore, in the present embodiment, in determining the three-dimensional shape of the measured region 108 with no strain, the two gauge points were defined in the X direction within the measured region 108 so as to be located at the two positions of the maximum height in the Z direction across the minimum height in the Z direction. However, the present invention is not limited thereto. For example, in choosing the two gauge points, the frequency property of an undulating surface shape may be used to identify a characteristic place so as to determine that place as the gauge point. Furthermore, gauge points can be specified at three or more positions in the measured region, so that the distance between the gauge points may be measured to determine strain. In this case, a strain distribution can be determined in the measured region. Thus, since the strain distribution within the measured region can be evaluated in relation to the surface shape, the mechanical properties of the micromaterial can be grasped in greater detail.

Furthermore, in the present embodiment, the measurement unit 150 includes the second objective lens 168, the focal position of which is aligned with that of the first objective lens 166 in the optical axis direction and automatically adjusted from the image-forming state of the measured region 108 on the CCD camera 170. However, the present invention is not limited thereto. For example, if the first objective lens and the second objective lens have a constant positional relation even with different focal positions in the optical axis direction, the focal positioning of the first objective lens on the micromaterial can be quickly performed.

Furthermore, in the present embodiment, the measurement unit 150 also includes the laser processing unit which emits a laser beam capable of shaping the micromaterial 102. However, the present invention is not limited thereto. The laser processing unit may be eliminated, and the micromaterial may be held in the strain generation unit with the reinforcing portions already cut. In this case, the elimination of the laser processing unit can contribute to a further reduction in the costs of the entire apparatus. The micromaterial may be processed by other techniques such as by electrical discharge processing, chemical processing, focused ion beam processing, or electron beam processing.

Furthermore, in the present embodiment, the strain generation unit 130 includes the two the chuck portions 134 and 136 for holding the micromaterial 102, and one chuck portion 134 (136) can be positioned relative to the other 136 (134) in the mutually orthogonal three axis directions. The micromaterial 102 is held with the retainer members 134 and 136. However, the present invention is not limited thereto. For example, the retaining members may not need to be employed but simply an adhesive may be used for securing purposes. In this case, the chuck portions can be positioned according to the hardening property of the adhesive, thereby adjusting the condition of the micromaterial being held. Or, the chuck portions may not be relatively adjustable in the aforementioned three axis directions. In that case, parts count can be reduced, so that further reductions in costs of the entire apparatus can be promoted.

Furthermore, in the present embodiment, the strain generation unit 130 is also configured to be movable within a plane orthogonal to the optical axis direction and tiltable relative to the optical axis direction. However, the present invention is not limited thereto. For example, the strain generation unit may be configured to be movable only within a plane orthogonal to the optical axis direction. In this case, the adjustment of the inclination of the micromaterial can be eliminated. Since this can reduce the man-hour for adjusting the micromaterial and parts count, the entire apparatus can be provided at further reduced costs. Or, the strain generation unit may be tiltable only relative to the optical axis direction. In this case, since parts count can be reduced while the shape of the micro region is measured at high speeds with high accuracy, the entire apparatus can be provided with further reduced costs. Or alternatively, the strain generation unit may not be movable within a plane orthogonal to the optical axis direction or tiltable relative to the optical axis direction. In that case, parts count can be further reduced, and thus the entire apparatus can be provided at further reduced costs.

Furthermore, in the present embodiment, a certain displacement is imparted between the chuck portions 134 and 136 to apply tensile stress to the micromaterial 102, and then after a temporary halt, the three-dimensional shape is measured. However, the present invention is not limited thereto. For example, the micromaterial may be distorted at a constant speed, thereby continuously applying tensile stress or compressive stress to the micromaterial. In that case, when the constant speed is equal to a certain strain speed (for example, 0.01/second or less), the thermal equilibrium state caused by the deformation of the micromaterial can be maintained at a constant state. It is thus possible to make a measurement with improved accuracy. Furthermore, even when tensile stress or compressive stress is different depending on the strain speed (deformation speed) (for example, as observed in high-temperature deformation or deformation of lead at room temperature), the certain constant strain speed makes it possible to determine tensile stress or compressive stress with improved accuracy.

Industrial Applicability

The present invention is applicable to the evaluation of mechanical properties of submicron to micron areas of a thin film material for development and manufacture of MEMS devices as well as for development and manufacture of MEMS materials including metal, ceramics, and polymer.

This application claims the priority benefit of Japanese Patent Application No. 2010-127109 filed on Jun. 2, 2010, which is hereby incorporated in its entirety by reference.

Reference Signs List
- 100 micromaterial strain measurement apparatus
- 102 micromaterial
- 104 support base
- 104A grip portion
- 104B shoulder portion
- 104C parallel portion
- 104D reinforcing portion
- 106 thin film
- 108 measured region
- 110, 132 base plate
- 112 bracket
- 114 positioning unit
- 116, 138 Y stage
- 118, 142 X stage
- 120 θ stage
- 122 β stage
- 124 α stage
- 130 strain generation unit
- 134, 136 chuck portion
- 140 inching X stage
- 144, 152 Z stage
- 146 load cell
- 150 measurement unit
- 154 lens barrel
- 156 white light source
- 158 reflective mirror
- 160, 166C half mirror
- 162 slider
- 164 inching Z stage
- 166 first objective lens
- 166A holder
- 166B lens
- 166D reference mirror
- 168 second objective lens
- 170 CCD camera

The invention claimed is:

1. A micromaterial strain measurement apparatus, comprising: a strain generation unit for applying tensile stress or compressive stress to a micromaterial so as to generate strain on the micromaterial and measuring the tensile stress or compressive stress, and a measurement unit for measuring deformation of the micromaterial due to the strain, wherein:

the measurement unit includes: a white light source for irradiating a measured region of the micromaterial; a two-dimensional photoelectric sensor for detecting interference light, the interference light being formed with a measurement beam of light from the measured region irradiated with the white light source and a reference beam of light from a reference mirror irradiated with light split from the white light source; a first objective lens which allows the two-dimensional photoelectric sensor to receive the interference light and includes the reference mirror; a second objective lens which has a constant positional relation with the first objective lens in an optical axis direction of the first objective lens, moved with the first objective lens, focal position of which is automatically adjusted from an image-forming state of the measured region on the two-dimensional photoelectric sensor, and replaceable with the first objective lens on the optical axis; and an image processing apparatus for measuring a three-dimensional shape of the measured region from a position of the first objective lens, at which the interference light provides the maximum contrast by relative scanning of the first objective lens in the optical axis direction and for defining a plurality of gauge points on the basis of the three-dimensional shape, the gauge points being reference positions for measuring a displacement of the measured region, the image processing apparatus further measuring a distance between the plurality of gauge points;

the strain generation unit includes: two chuck portions for holding the micromaterial; stress detection means for supporting one of the two chuck portions and measuring the tensile stress or compressive stress; and a moving mechanism for generating the strain by changing the distance between the two chuck portions; and the position of the first objective lens is determined initially on the optical axis on the basis of the position of the second objective lens which has been automatically adjusted, when the moving mechanism generates the strain on the micromaterial, the strain against the tensile stress or compressive stress is measured on the basis of the tensile stress or compressive stress measured by the stress detection means and the distance between the plurality of gauge points which have been followed, identified, and measured without missing the plurality of gauge points varied due to the strain by relatively scanning the first objective lens from the position initially determined in the optical axis direction.

2. The micromaterial strain measurement apparatus according to claim 1, wherein the strain is true strain which is determined from the distance between the plurality of gauge points in the absence of the strain and the distance between the plurality of gauge points in the presence of the strain.

3. The micromaterial strain measurement apparatus according to claim 1, wherein the plurality of gauge points are three or more.

4. The micromaterial strain measurement apparatus according to claim 1, wherein the measurement unit further includes a laser processing unit which emits a laser beam capable of shaping the micromaterial.

5. The micromaterial strain measurement apparatus according to claim 1, wherein one of the two chuck portions can be positioned relative to the other in mutually orthogonal three axis directions.

6. The micromaterial strain measurement apparatus according to claim 1 wherein the strain generation unit is movable within a plane orthogonal to the optical axis direction and tiltable relative to the optical axis direction.

7. A micromaterial strain measurement method for determining strain by applying tensile stress or compressive stress to a micromaterial so as to generate strain on the micromaterial, measuring the tensile stress or compressive stress, and measuring deformation of the micromaterial caused by the strain, the method including the steps of:

holding the micromaterial;

automatically adjusting a focal position of a second objective lens from an image-forming state of a measured region of the micromaterial by moving the second objective lens on an optical axis;

replacing the second objective lens with a first objective lens which has a constant positional relation with the second objective lens, includes a reference mirror, and moves with the second objective lens in the optical axis direction;

initially determining the position of the first objective lens on the basis of the position of the second objective lens on the optical axis;

generating the strain on the micromaterial being held and measuring the tensile stress or compressive stress;

irradiating the measured region of the micromaterial, to which the strain has been imparted, with light from a white light source;

allowing a two-dimensional photoelectric sensor to receive interference light through the first objective lens including the reference mirror, the interference light being formed with a measurement beam of light from the measured region and a reference beam of light from the reference mirror irradiated with light split from the white light source;

relatively scanning the first objective lens from the position initially determined in the optical axis direction thereof and measuring a three-dimensional shape of the measured region from a position of the first objective lens at which the interference light provides a maximum contrast;

measuring a distance between a plurality of gauge points, on the basis of the measured three-dimensional shape, by following and identifying without missing a plurality of the gauge points, which serve as a reference position when measuring a displacement of the measured region changed due to the strain; and measuring the strain against the resulting tensile stress or compressive stress on the basis of the resulting distance between the plurality of the gauge points and the tensile stress or compressive stress.

8. The micromaterial strain measurement method according to claim 7, including the step of continuously applying the tensile stress or compressive stress to the micromaterial by deforming the micromaterial at a constant speed.

* * * * *